United States Patent [19]

Tahara

[11] Patent Number: 5,446,174
[45] Date of Patent: Aug. 29, 1995

[54] 1-β7,8-TRIHYDROXY VITAMIN $D_2$, 1β7,8-TRIHYDROXY VITAMIN $D_3$, AND DERIVATIVES THEREOF

[75] Inventor: Yuji Tahara, Sapporo, Japan

[73] Assignee: Hoxan Corporation, Hokkaido, Japan

[21] Appl. No.: 104,565

[22] Filed: Aug. 11, 1993

Related U.S. Application Data

[60] Division of Ser. No. 879,735, May 6, 1992, Pat. No. 5,283,345, which is a continuation of Ser. No. 571,535, Aug. 29, 1990, abandoned.

[30] Foreign Application Priority Data

Mar. 9, 1988 [JP] Japan .................................. 63-55342

[51] Int. Cl.$^6$ .................... C07D 317/20; C07C 401/00
[52] U.S. Cl. ..................................... 549/214; 549/336; 552/653
[58] Field of Search ........................ 568/819; 560/256; 556/445, 446, 449; 549/336, 214; 552/586

[56] References Cited

U.S. PATENT DOCUMENTS 4,755,329  7/1988  DeLuca et al. ..................... 549/415

OTHER PUBLICATIONS

D. Desmaele et al., "Synthesis of A-ring of 1S-hydroxykohlcalciferol", *Tetrahedron Letters*, vol. 26, No. 44, pp. 4941–4944 (1985).

J. Miguel Aurrecoechea et al., "A Short, Enantiospecific Synthesis of the 1α-Hydroxyvitamin D Enyne A-Ring Synthon," *Tetrahedron Letters*, vol. 28, No. 42, pp. 4947–4950 (1987).

Hector F. DeLuca et al., "Vitamin D: Recent Advances", *Ann. Rev. Biochem.*, 52: 411–419 (1983).

Roselyne Pardo et al., "Synthese des metabolites de la vitamine D", *Bulletin De La Societe Chimque De France*, No. 1, pp. 11–98 –11–114 (1985).

Nubuo Ikegawa et al., "Synthesis of Active Forms of Vitamin D(I)–Recent Advances," *Organic Synthetic Chem.*, 37: pp. 755–770 (1979).

Martin J. Calverley, "Synthesis of MC 903, A Biologically Active Vitamin D Metabolite Analogue," *Tetrahedron Lts.* vol. 43, No. 20, pp. 4609–4619 (1987).

B. Lythgoe, "Synthetic Approaches to Vitamin D and its Relatives," *Chem. Soc. Rev.*, 9, pp. 449–475 (1980).

*Primary Examiner*—Nicky Chan
*Attorney, Agent, or Firm*—Foley & Lardner

[57] ABSTRACT

There are disclosed novel compounds that can be used to derive therefrom a fragment that corresponds to an A-ring which is to be combined with fragments which respectively correspond to C- and D-rings in synthetic formation of vitamin $D_3$ derivatives by cleaving the 7,8-bondings by means of oxidizing agents following any known process. According to the invention, there is provided an industrially efficient and effective method of manufacturing above compounds that utilizes allylic hydroxylation to add an oxygen function group to position C(1), a method which is completely different from any existing synthetic methods.

1 Claim, No Drawings

1-β,7,8-TRIHYDROXY VITAMIN D₂, 1β,7,8-TRIHYDROXY VITAMIN D₃, AND DERIVATIVES THEREOF

This application is a divisional of application Ser. No. 07/879,735, filed May 6, 1992, now U.S. Pat. No. 5,283,345 which is a continuation of application Ser. No. 07/571,535 filed Aug. 29, 1990, now abandoned.

FIELD OF THE INVENTION

This invention relates to $1\beta,7,8$-trihydroxy vitamin $D_2$, $1\beta,7,8$-trihydroxy vitamin $D_3$, their novel derivative compounds and a method of manufacturing these chemicals from 7,8-dihydroxy vitamin $D_2$, 7,8-dihydroxy vitamin $D_3$ or any of their derivatives.

BACKGROUND OF THE INVENTION

The fact that vitamin D plays a vital role in formation of bones as it regulates absorption of calcium and reabsorption of bone inorganic substances by intestine has recently been made known by an extensive research on metabolites of bone (H. F. DeLuca et al., Ann. Rev. Biochem., vol. 52. p. 411, 1983).

It has also been known that some vitamin $D_3$ derivatives have the function of inducing cell differentiation, suggesting enormous potential applications of vitamin D in the future (T. Suda et al., Bone & Mineral Res./4. ed. W. A. Peck, Elsevier, Amsterdam, p. 1, 1986) .

1α, 25-dihydroxty vitamin $D_3$ (N. Ikegawa et al., Organic Synthetic Chemistry, vol. 37, p. 755, 1979) and 1α-hydroxy vitamin $D_3$ (C. Kaneko, Organic Synthetic Chemistry, vol. 33, p 75, 1975) which are chemically analogous to each other and actively substantiate the above described effects have been attracting attention and are currently used as medicines for diseases such as chronic nephric insufficiency, while the latter has proved to be an excellent medicine for curing osteoporosis.

Under these circumstances, researches have been actively conducted on synthetic preparation of derivatives of 1α-hydroxy vitamin $D_3$ which are, regarded as indispensable for substantiating biogenic activities (B. Lythgoe, Chem. Soc. Rev., vol. 9, p. 449, 1980; R, Pardo et al., Bull. De La Soc. Chim. De Fr. p. 98, 1985).

Currently, the process of synthesis of derivatives of 1α-hydroxy vitamin $D_3$ typically starts with synthesis of 1α-hydroxylated steroid, which is converted to corresponding 1α-hydroxy-5,7 dienesterol and then to the intended vitamin D derivative by using known photochemical techniques. However, this known process comprises a number of steps, making the overall processes rather inefficient. (See above-cited C. Kaneko's paper.)

With a view to overcome these problems, a number of improved processes have recently been proposed, which can be categorized into the following three groups or groups (a), (b) and (c).

Group (a)
1) direct hydroxidation of vitamin $D_3$ and related compounds at C(1); H. F. De Luca et al., J. Org. Chem., vol. 45, p. 3253, 1980
2) preparation of 1α-hydroxylated compounds; H. F. De Luca et at., Japanese Patent Application No. 54-555366
3) derivatives of cyclovitamin D; H. F. De Luca et al., Japanese Patent Application No. 57-206229
4) derivatives of 1α-hydroxycyclo vitamin D; H. F. De Luca et at., Japanese Patent Application No. 57-206230
5) derivatives of 1-oxocyclo vitamin D; H. F. De Luca et al., Japanese Patent Application No. 57-206231

In any of the group (a) processes, a vitamin D derivative is converted to a derivative of 3,5-cyclovitamin D, which is then combined with an allylic acid at positon C(1), said compound being further coverted to a derivative of vitamin D.

Group (b)
1) direct-positional or stereoselective α-hydroxylation of a (5E)-calciferol derivative; R. H. Hesse et al., J. Org. Chem. , vol. 51 , p. 1635, 1986
2) synthesis of 25-hydroxy vitamin $D_3$ and 1α,25-dihydroxy vitamin $D_3$ from vitamin $D_2$; R. H. Hesse et al., J. Org. Chem., vol. 51 , p. 4819, 1986
3) synthesis of MO-903, a metabolite of biogenetic vitamin D; M. J. Calverley, Tetrahedron, vol. 43, p. 4609, 1987

Any of the group (b) research papers proposes a process where vitamin D is temporarily combined with allylic acid at position C(1) to convert it to transvitamin D, which is then reconverted to vitamin.

Group (c)
1) Synthesis of A-ring of 1S-hydroxykohlcalciferol; D. Desmaele et al., Tetrahedron Letters, vol. 16, p. 4941, 1985
2) Improved synthesis of an A-ring of 1 a ,25dihydroxy vitamin D; L. Castedo et al., Tetrahedron Letters, vol 28, p. 2099, 1987
3) Stereoselective synthesis of Lynthgoe A-ring aldehyde for synthesis of 1α-hydroxytachysterol and calciferol; E. G. Baggiolini et al., Tetrahedron Letters, vol. 28, p. 2095, 1987
4) simplified synthesis of Enyne A-ring of 1α-hydroxy vitamin D; W. H. Okamura et al., Tetrahedron Letters, vol. 28, p. 4947, 1987
5) stereoselective synthesis of 1α, 25-dihydroxykohlcalciferol and 1α,25-dihydroxyergocalciferol; E. G. Baggiolini et al., J. Org. Chem. vol. 51, p. 3098, 1986
6) ergocalciferol derivatives; E. G. Baggiolini et al., Japanese Patent Application No. 59-52417
7) calcifenol derivatives; E. G. Baggiolini et al., Japanese Patent Application No. 60-22091

Group (c) represents efforts to attain a totally synthetic process in which a chemical fragment that corresponds to an A-ring having a hydroxyl group at C(1) position is synthesized, to which fragments that correspond to a C-ring and a D-ring are combined to obtain the aimed compounds. However, such a process consists of a number of steps and hence does not provide a simple, economic and satisfactory method of manufacturing the compounds in practical applications. Moreover, compounds which are obtained by such a process do not necessarily exhibit satisfactory chemical effects.

It is therefore an object (the first object) of the present invention to provide novel and chemically useful $1\beta,7,8$-trihydroxy vitamin $D_2$, $1\beta,7,8$-trihydroxy vitamin $D_3$ and their derivatives.

It is another object (the second object) of the present invention to provide an industrially efficient and effective method of manufacturing above chemicals by directly combining vitamin $D_2$, vitamin $D_3$ or any of their derivatives with an oxygen function group at position C(1) through utilization of allylic hydroxylation as described later, a method which is completely different from any exisiting synthetic methods in terms of basic concept and practical applications.

DISCLOSURE OF THE INVENTION

The first object of the present invention is achieved by providing a chemical compound characterized by that it is expressed by formula

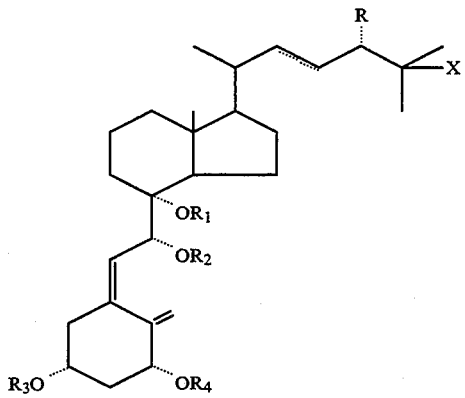

(where R represents a hydrogen atom and the dotted line shown as a side chain represents an additional C—C bond or R represents a methyl group and the dotted line shown as a side chain represents an additional C—C bond whichever the case may be;

$R_1$, $R_2$, $R_3$ and $R_4$ represent not necessarily identically a hydrogen atom or a hydroxy protecting group; and X represents a hydrogen atom, a hydroxy group or its derivative.)

The above described compound provided to achieve the first object of the invention is a novel compound that can be used for easily deriving therefrom a fragment that corresponds to a A-ring to be used for combining it with fragments that correspond to a C-ring and a D-ring by cleaving its 7,8 linkage by means of a known technique in an oxidizing environment.

The second object of the invention is achieved by providing a method characterized by that said method is effectively used for manufacturing 1β,7,8-trihydroxy vitamin $D_2$, 1β,7,8-trihydroxy vitamin $D_3$ and their derivatives expressed by formula [II]

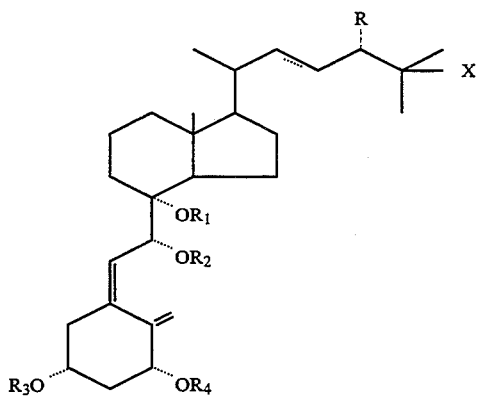

(where R represents a hydrogen atom and the dotted line shown as a side chain represents an additional C—C bond or R represents a methyl group and the dotted line shown as a side chain represents an additional C—C bond whichever the case may be;

$R_1$, $R_2$, $R_3$ and $R_4$ represent not necessarily identically a hydrogen atom or a hydroxy protecting group; and X represents a hydrogen atom, a hydroxy group or its derivative.)

wherein 7,8-dihydroxy vitamin $D_2$, 7,8-dihydroxy vitamin $D_3$ or any of their derivatives expressed by formula [I]

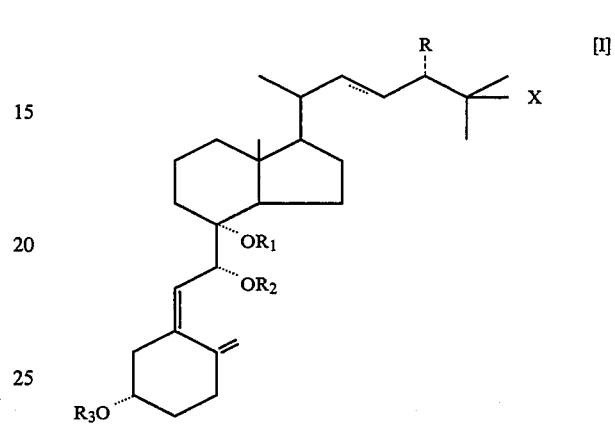

(where R represents a hydrogen atom and the dotted line shown as a side chain represents an additional C—C bond or R represents a methyl group and the dotted line shown as a side chain represents an additional C—C bond whichever the case may be;

$R_1$, $R_2$ and $R_3$ represent not necessarily identically a hydrogen atom or a hydroxy protecting group; and X represents a hydrogen atom, a hydroxy group or its derivative.)

is subjected to allylic hydroxylation by using a metal oxide such as selenium dioxide or a metal peroxide in an inactive solvent.

The method according to the invention can be used for effectively manufacturing the above cited chemical compounds on industrial basis as compared with known methods because an oxygen functional group is added to C1-position by means of alltylic acid that chemically advantageously affects the process of addition.

PREFERRED EMBODIMENTS OF THE INVENTION

Compounds represented by formula [I] that can be used with the manufacturing method of the invention include the following known chemicals, 7,8-dihydroxy-7,8-dihydro vitamin $D_3$ ($R_1=R_2=R_3=H$) , 3β-O-(t-dibutyldimethylsilyl)-7,8-dihydroxy-7,8-dihydro vitamin $D_3$ ($R_1=R_2=H$, $R_3=S_2.+Bu'(Me)_2$) [W. H. Okamura et al. , J. Org. Chem., vol. 48, p. 1414, 1983], 7,8-dihydroxy vitamin $D_2$ ($R_1=R_2=R_3=H$, R=Me, with a side chain) [Y. Wang et al. , Acta. Chim. Sin., vol. 24, p. 126, 1958] and 7,8,25-trihydroxy vitamin $D_3$ derivatives ($R_2=R_2=R_3=H$ or hydroxy protecting group, R=H, X=$OR_4$ and $R_4=H$ or hydroxy protecting group, without a side chain) [H. F. Luca et al., Japanese Patent Application No. 59-93130].

A compound expressed by formula [1] is subjected to allylic hydroxylation by using a metal oxide such as selenium dioxide or a metal peroxide in an inactive solvent such as methyl chloride or acetonitrile to produce a novel compound by the manufacturing method according to the invention which is expressed by formula [II] quoted above.

The aimed compound (expressed by formula [II] can be separated from the reaction system by any ordinary technique. For example, after completion of the reaction, the reaction system may be washed with alkaline water solution and thereafter with water and then dried to remove the solvent and the residue may be subjected to a process color chromatography.

Moreover, a compound expressed by formula [II] can be advantageously used to derive therefrom a fragment which corresponds to an A-ring which is to be combined with fragments which respectively correspond to C- and D-rings in the synthetic methods of forming vitamin D3 derivatives described earlier with reference to group (c) by cleaving the 7,8 bondings by means of oxidizing agents following any known method. (See W. Wang et al., Acta, Chim. Sin., vol. 24, p. 126, 1958; and W. H. Okamura, ibid.)

Now the present invention will be described in greater detail by referring to a number of examples, in which "vitamin D" refers to "vitamin $D_2$" or "vitamin $D_3$" and the spectrum values are those of vitamin $D_3$.

EXAMPLE 1

"Preparation of 7,8-dihydroxy-7,8-dihydro vitamin D 7,8-acetonide"

A 400mg of 7,8-dihydroxy-7,8-dihydro vitamin D and 0.5 ml of 2,2-dimethoxypropane were dissolved in 5 ml of dry methylene chloride. Stirring the solution at 0° C., camphor sulfonic acid was added thereto by an amount good for a catalyst.

The solution was stirred for another two hours at room temperature and the reaction products were diluted with 20 ml of methylene chloride and washed sequentially by saturated water solution of sodium hydrogencarbonate and water. Thereafter the residue was dried by sodium sulfate.

The residual product which was free from the solvent was then subjected to a process of silica gel column chromatography to obtain 7,8-dihydroxy-7,8-dihydro vitamin D 7,8-acetonide.

The above reaction is expressed by the following formulas.

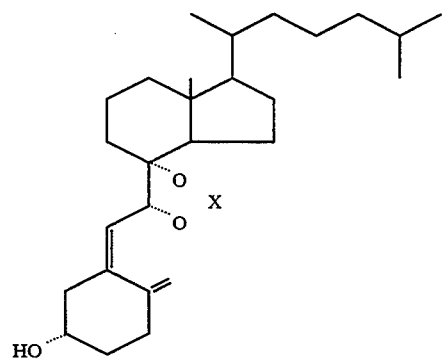

IR spectrum: $\nu$ max $(CHCl_3)cm^{-1}$: 3400

NMR spectrum: $(CCl_4)$ $\delta$: 0.53 (3H, S), 0.87(9H, d, J=6 Hz), 1.19 (3H,S), 1.30(3H,S), 3.30–3.80(1H,m), 4.60 (1H,d,J=10 Hz), 4.96(1H,brs), 5.46(1H,d, J=10 Hz)

mass spectrum: (FD)m/e; 459($M^-$+1), 458($M^-$), 443, 400, 383

EXAMPLE 2

"Preparation of 3$\beta$-O-(t-butyldimethylsilyl)-7,8-dihydroxy-7,8-dihydro vitamin D 7,8-acetonide"

A 450 mg of 7,8-dihydroxy-7,8-dihydro vitamin D 7,8-acetonide and 300 mg of imidazole were dissolved in 30 ml of dry dimethylformamide and then 300 mg of t-butyldimethylmyrilchloide was added thereto while the solution was being stirred at 0° C.

The solution of the reaction products was stirred for another two hours at room temperature and then diluted by 100 ml of methylene chloride. The diluted solution was washed sequentially by water, 10% hydrochloric acid, saturated aqueous solution of sodium hydrogencarbonate and water and the residue obtained by removing the solvent was subjected to a process of silca gel column chromatography [silica gel 6 g, solvent; n-hexane-ethyl acetate (100:1 v/v)] to get 500 mg of 3$\beta$-O-(t-butyldimethylsiryl)-7,8-dihydroxy-7,8-dihydro vitamin D 7,8-acetonide.

The above reaction is expressed by the formulas shown below.

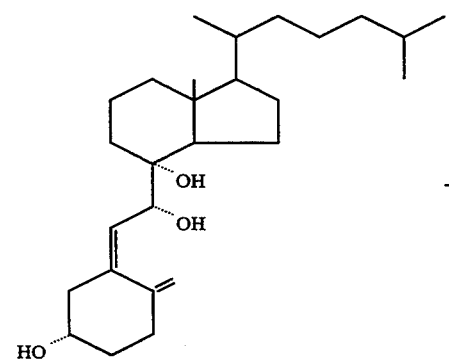 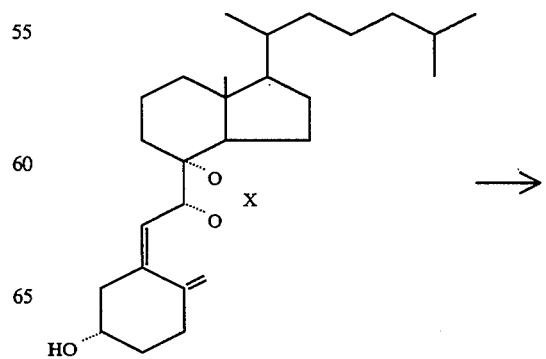

-continued

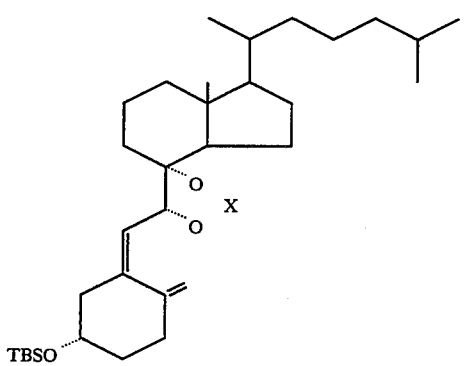

NMR spectrum: (CCl₄) δ: 0.06(6H, S), 0.53(3H, S), 0.85 (9H,d,J=6 Hz), 0.93(9H,S), 1.20(3H,S), 1.30 (3H,S), 3.4–3.8(1H,m), 4.60(1H,d,J=10 Hz), 5.00(2H,brs), 5.45(1H,d,J=10 Hz)

mass spectrum: (FD)m/e; 573(M⁻+1), 572(M⁻, 557, 514, 457, 439

EXAMPLE 3

"Preparation of 3β-O-(t-butyldimethylsilyl)-7,8-dihydroxy-7,8-dihydro-1β-hydroxy vitamin D 7,8-acetonide by oxidation of 3β-O-(t-buthyldimethylsilyl)-7,8-dihydroxy-7,8-dihydro vitamin D 7,8-acetonide"

(a) A 100 mg of 3β-O-(t-butyldimethylsilyl)-7,8-dihydroxy-7,8-dihydro vitamin D 7,8-acetonide was dissolved in 20 ml of dry methylene chloride, to which 70 mg of selenium dioxide was added and the solution was heated for 20 hours for reflux while it was being stirred.

After completion of the reaction, the solution was filtered by cerite and washed sequentially by 10% aqueous solution of sodium hydroxide and water. The product was dried by sodium sulfate and the residue obtained by removing the solvent was subjected to a process of silica gel column chromatography [silica gel 1 g, solvent; n-hexane-ethyl acetate (100:5 v/v)] to get 55 mg of 3β-O-(t-butyldimethylsilyl)-7,8-dihydroxy-7,8-dihydro-1β-hydroxy vitamin D 7,8-acetonide.

IR spectrum: ν max (CHCl₃)cm⁻¹: 3400

NMR spectrum: (CCl₄)δ: 0.09(6H,S), 0.53(3H,S), 0.87(9H,d, J=6 Hz), 0.93 (9H, S), 1.20 (3H, S), 1.30 (3H, S), 3.60–4.10(1H,m), 4.60(1H,d,J=10 Hz), 5.16(1H, brs), 5.28 (1H, brs), 5.58 (1H, d, J=10 Hz)

mass spectrum (FD)m/e; 589(M⁻+1), 588(M⁻), 573, 530, 513, 473, 455, 324

(b) A 100 mg of 3β-O-(t-butyldimethylsilyl)-7,8-dihydroxy-7,8-dihydro vitamin D 7,8-acetonide was dissolved in 20 ml of dry methylene chloride, to which 10 mg of selenium dioxide and 2 ml of 3 mol toluene solution of t-butylhydroperoxide were added while it was being heated and stirred for 20 hours for reflux.

After completion of the reaction, the product was 50 mg of 3β-O-(t-butyldimethylsilyl)-7,8-dihydroxy-7,8-dihydro-1β-hydroxy vitamin D 7,8-acetonide.

(c) A 100 mg of 3β-O-(t-butyldimethylsilyl)-7,8-dihydroxy-7,8-dihydro vitamin D 7,8-acetonide was dissolved in 20 ml of dry methylene chloride, to which 10 mg of selenium dioxide and 2 ml of 3 mol toluene solution of t-butylhydroperoxide as well as an amount of salicylic acid good for a catalyst were added while it was being heated and stirred for 20 hours for reflux.

After completion of the reaction, the product was treated similarly as in the case of (a) above to obtain 47 mg of 3β-O-(t-butyldimethylsilyl)-7,8-dihydroxy-7,8-dihydro-1β-hydroxy vitamin D 7,8-acetonide.

(d) 100 mg of 3β-O- (t-butyldimethylsilyl) -7,8-dihydroxy-7,8-dihydro vitamin D 7,8-acetonide was dissolved in 20 ml of dry methylene chloride, to which 70 mg of selenium dioxide and an amount of salicylic acid good for a catalyst were added. The mixture was heated and stirred for 20 hours for reflux.

After completion of the reaction, the product was treated similarly as in the case of (a) above to obtain 45 mg of 3β-O-(t-butyldimethylsilyl)-7,8-dihydroxy-7,8-dihydro-1β-hydroxy vitamin D 7,8-acetonide.

The reactions (a) through (d) above are equally expressed by the formulas below.

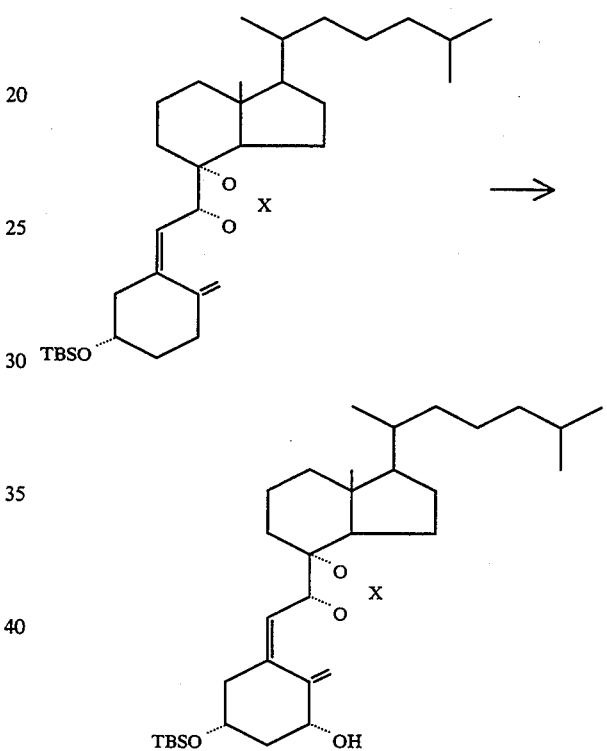

EXAMPLE 4

"Preparation of 3β-acetoxy-3β-O-(t-butyldimethylsilyl)-7,8-dihydroxy-7,8-dihydro vitamin D 7,8-acetonide"

A 30 mg of 3β-O-(t-butyldimethylsilyl)-7,8-dihydroxy-7,8-dihydro-1β-hydroxy vitamin D 7,8-acetonide was dissolved in 1ml of dry pyridine, to which 10 mg of acetyl-chloride was added while the solution was being stirred at 0° C.

The mixture of the reaction products was diluted by 30 ml of methylene chloride and the diluted solution was stirred for four hours, which was then washed sequentially with water, 10% hydrochloric acid, saturated aqueous solution of sodium hydrogencarbonate and water and dried by sodium sulfate. Thereafter, the solvent was removed from the solution and the residue was subjected to a process of silica gel column chromatography [silica gel 1 g, solvent; n-hexane-ethyl acetate (100:1 v/v)] to obtain 29 mg of 1β-acetoxy-3β-O-(t-butyldimethylsilyl)-7,8-dihydroxy-7,8dihydro vitamin D 7,8-acetonide.

IR spectrum: ν max (CHCl₄) δ: 0.10 (6H, S), 0. 56 (3H, S), 0.88 9H,d,J=6 Hz), 0.93(9H,S), 1.20(3H,S), 1.30(3H,S), 2.10(3H,S), 3.5–4.0(1H,m), 4.57(1H,d,J=10 Hz), 4.80–5.20(1H,m), 4.95 (1H,brs), 5.60(1H,d,J=10 Hz)

mass spectrum: (FD)m/e; 630(M⁻), 615, 573, 515, 366

The above reaction is expressed by the following formulas.

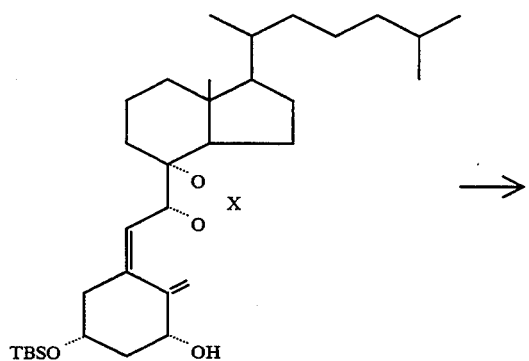

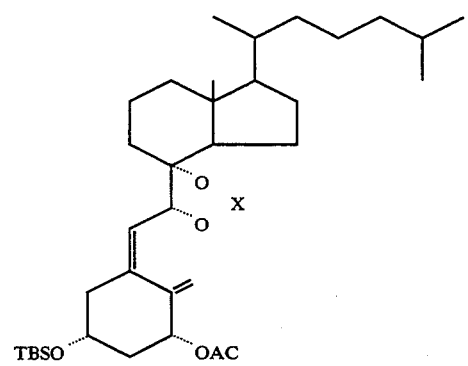

EXAMPLE 5

"Preparation of 7,8-dihydroxy-7,8-dihydro-1β-hydroxy-vitamin D 7,8-acetonide"

(a) An amount of pyridinium-paratoluenesulfonate good for a catalyst was added to 100 mg of 3β-O-(t-butyldimethylsilyl)-7,8-dihydroxy-7,8-dihydro-1β-hydroxy vitamin D 7,8-acetonide dissolved in 30 ml of methanol and the solution was heated and stirred for 10 hours for reflux.

After completion of the reaction, the solvent was removed and the residue was solved in 30 ml of chloroform. After washing the solution with water, it was dried by sodium sulfate and the solvent was removed. The product was subjected to a process of silica gel column chromatography (silica gel ]g, solvent; chloroform) to obtain 90 mg of 7,8-dihydroxy-7,8-dihydro-1β-hydroxy vitamin D 7,8-acetonide.

IR spectrum: ν max (CHCl₄)cm⁻¹: 3400

NMR spectrum: (CCl₄)δ: 0.5 (3H,S), 0.88(9H,d,J=6 Hz), 1.20 (3H,S), 1.33 (3H, S), 3.50–4.30(2H,m), 4.70 (1H,d,J=10 Hz), 5.05(1H,brs), 5.25(1H,brs) 5.70(1H,d,J=10 Hz)

mass spectrum: (FD)m/e; 475(M⁻+1), 474(M⁻), 459, 416, 399

(b) 100 mg 3β-O-acetyl-1β-acetoxy-7,8-dihydroxy-7,8-dihydro vitamin D 7,8-acetonide was dissolved with an amount of paratoluene sulfonic acid good for a catalist in 30 ml of methanol and the solution was stirred for 10 hours.

After completion of the reaction, the catalyst was removed from the mixture of the reaction products the residue was dissolved in 50 ml of methylene chloride and then washed sequentially with saturated aqueous solution of sodium hydrogencarbonate and water. Thereafter, the product was dried by sodium sulfate.

The dried product was treated similarly as in the case of (a) to obtain 91 mg of 7,8-dihydroxy-7,8-dihydro-1β-hydroxy vitamin D 7,8-acetonide.

The reactions of Example 5 are expressed by the following formulas.

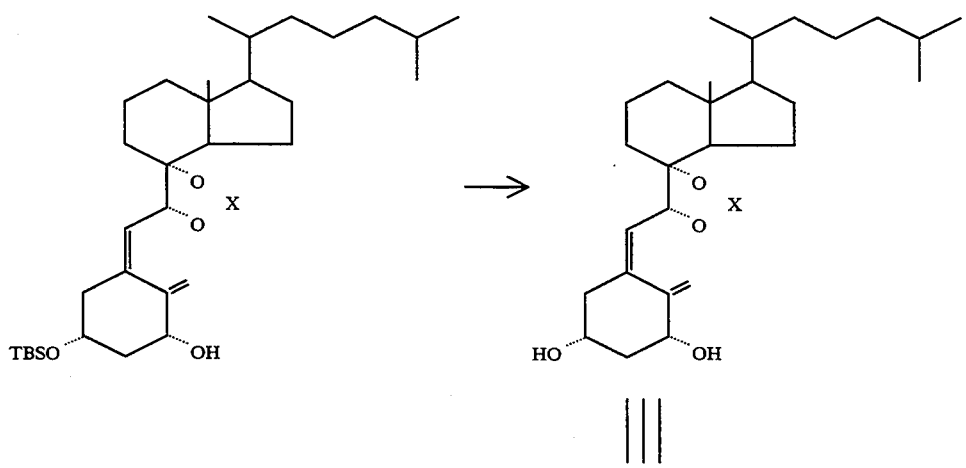

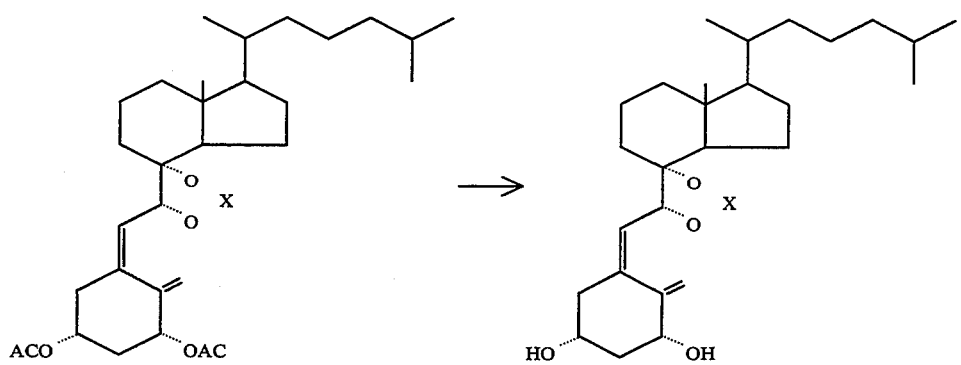

EXAMPLE 6

"Preparation of 3β-O-acetyl-1β-acetoxy-7,8-dihydroxy-7,8dihydro vitamin D 7,8-acetonide"

A 100 mg of 7,8-dihydroxy-7,8-dihydro-1β-hydroxy vitamin D 7,8-acetonide was dissolved in 2 ml of pyridine with an amount of 4-dimethylaminopyridine good for a catalyst and the 100 mg off acetylchloide was added to the solution while it was being stirred at 0° C. The solution was further stirred for two hours at room temperature and then diluted with 50 ml of methylene chloride. Afterward, it was washed sequentially with water, 10% hydrochloric acid, saturated aqueous solution of sodium hydrogencarbonate and water and then dried by sodium sulfate.

The residue after removing the solvent was subjected to a process of silica gel column chromatography [silica gel 1 g, solvent: n-hexane-ethyl acetate (100:1 v/v)] to obtain 102 mg of 3β-O-acetyl-1β-acetoxy-7,8-dihydroxy-7,8-dihydro vitamin D 7,8-acetonide.

IR spectrum: ν max (CHCl₃)cm⁻¹: 1730
NMR spectrum: (CCl₄) δ: 1.30(3H,S), 0.81 (9H,d,J=6 Hz), 1.20 (3H,S), 1.30(3H,S), 2.00(3H,S), 4.40–4.88 (1H,m), 4.90–5.30(1H,m), 4.60(1H,d,J=10 Hz) 5.00(1H,brs), 5.18(1H,brs), 5.68 (1 H, d,J=10 Hz)
mass spectrum: (FD) m/e; 558 (M⁻), 543, 501 , 294, 264

The reaction Example 6 is expressed by the following formulas.

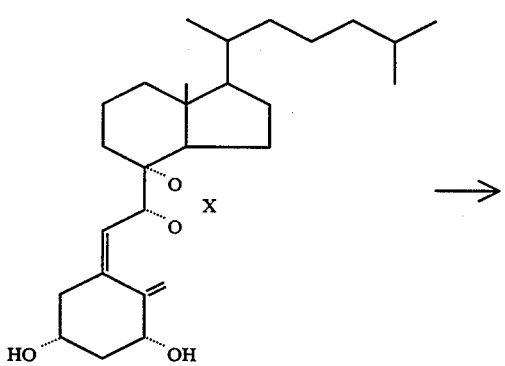

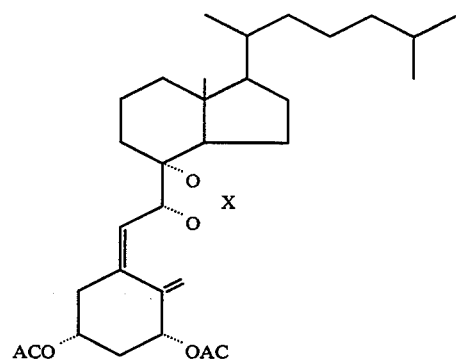

EXAMPLE 7

"3β-O-(t-butyldimethylsilyl)-7,8-dihydroxy-7,8-dihydro-1β-hydroxy vitamin D"

(a) A 100 mg of 3β-O-(t-butyldimethylsilyl)-7,8-dihydroxy-7,8-dihydro vitamin D was dissolved in 30 ml of dry methylene chloride, to which 100 mg of selenium dioxide was added. The solution was then heated and stirred for three days for reflux.

After completion of the reaction, the mixture of the reaction products was washed sequentially with 10% aqueous solution of sodium hydroxide and water and dried with sodium sulfate.

After removing the solvent, the residue was subjected to a process of silica gel column chromatography [silica gel 1 g, n-hexane-ethyl acetate (10:1 v/v)] to obtain 57 mg of 3β-O-(t-butyldimethylsilyl)-7,8-dihydroxy-7,8-dihydro-1β-hydroxy vitamin D.

IR spectrum: ν max (CHCl₃)cm⁻¹: 3400
NMR spectrum: (CCl₄) δ: 0.13(6H,S), 0.80(3H,S), 0.90(9Y,d, J=6 Hz), 0.95(9H,S), 3.90–4.30(2H,m), 4.75 (1H,d,J=1.0 Hz), 4.80(1H,brs), 5.60(1H,brs) 5.83(1H,d,J=10 Hz)
mass spectrum 8FD) m/e; 549 (M⁻+1), 548 (M⁻), 537 , 513, 473, 455, 283, 265

(b) A 100 mg of 3β-O-(t-butyldimethylsilyl)-7,8-dihydroxy-7,8-dihydro vitamin D was dissolved in 20 ml of dry acetonitrile, to which 60 mg of selenium dioxide was added. The solution was then heated and stirred for one hour for reflux.

After completion of the reaction, the solvent was removed from the mixture of the reaction products and the residue was dissolved in 50 ml. The solution was washed sequentially with 10% aqueous solution of sodium hydroxide and water and dried with sodium sulfate.

The product was treated similarly as in the case of above to obtain 12 mg of 3S-O-(t-butyldimethylsilyl)-7,8-dihydroxy-7,8-dihydro-1β-hydroxy vitamin D.

(c) The same amount of the reagents and that of the solvent as in (b) were made to react at room temperature for two days and then the product was treated in a similar manner to obtain 10 mg of 3β-O-(t-butyldimethylsilyl)-7,8-dihydroxy-7,8-dihydro-1β-hydroxy vitamin D from 100 mg of 3β-O-(5-butyldimethylsilyl)-7,8-dihydroxy-7,8-dihydro-vitamin D.

(d) A mixture containing the same amount of the reagents and that of the solvent as in (a) and a drop of water were heated for three days for reflux. The reaction product was treated similarly as in the case of (a) to obtain 55 mg of 3β-O-(t-butyldimethylsilyl)-7,8-dihydroxy-7,8-dihydro-1β-hydroxy vitamin D out of 100 mg of 3β-O-(t-butyldimethylsilyl)-7,8-dihydroxy-7,8-dihydro vitamin D.

(e) The same amount of the reagents and that of the solvent as in (a) were heated with 3 ml of acetonitrile for 13 hours for reflux. The reaction product was treated similarly as in the case of (a) to obtain 60 mg of 3β-O-(t-butyldimethylsilyl)-7,8-dihydroxy-7,8-dihydro-1β-hydroxy vitamin D out of 100 mg of 3β-O-(t-butyldimethylsilyl)-7,8-dihydroxy-7,8-dihydro vitamin D.

The reactions of Example 7 are expressed by the following formulas.

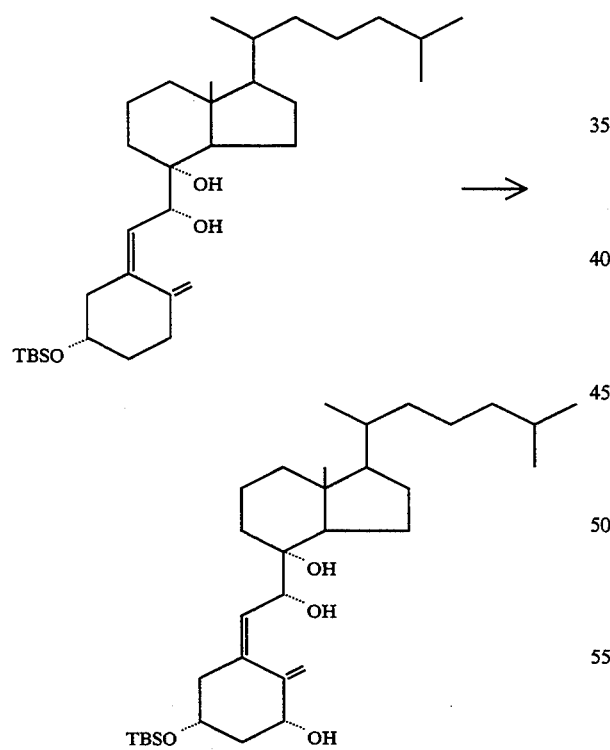

EXAMPLE 8

"Preparation of 3β-O-(t-butyldimethylsilyl)-7,8-dihydroxy-7,8-dihydro-1β-hydroxy vitamin D 7,8-acetonide by acetonidation of 3β-O-(t-butyldimethylsilyl)-7,8-dihydroxy-7,8-dihydro-1β-hydroxy vitamin D"

A 10 mg of 3β-O-(t-butyldimethylsilyl)-7,8-dihydroxy-7,8-dihydro-1β-hydroxy vitamin D and 0.1 ml of 2,2-dimethoxypropane were dissolved in 2 ml of methylene chloride and the solution was stirred at 0° C. with an amount of camphor sulfonic acid good for a catalyst. The solution was further stirred at room temperature for two hours and then diluted with 10 ml of methylene chloride. The diluted solution was washed sequentially with saturated aqueous solution of sodium hydrogencarbonate and water and dried by sodium sulfate.

After removing the solvent, the residue was subjected to a process of silica gel column chromatography [silica gel 0.5 g, solvent; n-hexane-ethyl acetate (100:1 v/v)] to obtain 10 mg of 3β-O-(t-butyldimethylsilyl)-7,8-dihydroxy-7,8-dihydro-1β-hydroxy vitamin D 7,8-acetonide. The product which had been obtained by the chemical equation as shown below was compared with the product Example 3 by means of the IR and NMR spectrum technique to find that the two products were chemically completely identical.

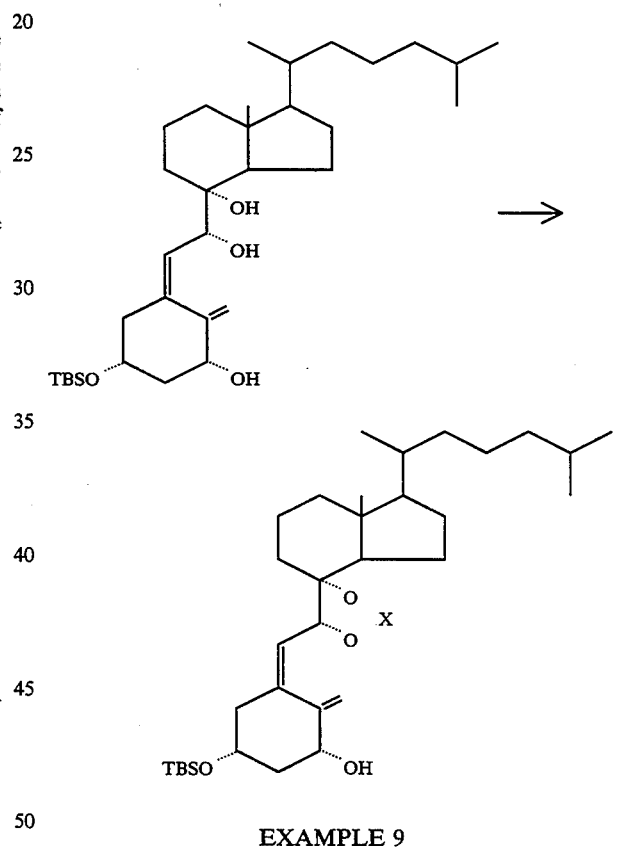

EXAMPLE 9

"Preparation of 3β-O-(t-butyldimethylsilyl)-7,8-dihydroxy-7,8-dihydro-1β-t-butyldimethylsilyloxy vitamin D"

A 92 mg of 3β-O-(t-butyldimethylsilyl)-7,8-dihydroxy-7,8-dihydro-1β-hydroxy vitamin D, 50 mg of imidazole and an amount of 4-dimethylaminopyridine good for a catalyst were dissolved in 2 ml of dry dimethylformamide and 50 mg of t-butyldimethylsilyl was added to the solution while it was being stirred.

After completion of the reaction, the solution of the reaction product was stirred for 24 hours at room temperature and was diluted with 50 ml of methylene chloride. The diluted solution was then washed sequentially with water, 10% hydrochloric acid, saturated aqueous solution of sodium hydrogencarbonate and water and later dried by sodium sulfate.

After removing the solvent, the residue was subjected to a process of silica gel column chromatography [silica gel 1 g, solvent; n-hexane-ethyl acetate (100:5 v/v)] to obtain 100 mg of 3β-O-(t-butyldimethylsilyl)-7,8-dihydroxy-7,8-dihydro-1β-t-butylmethylsilyl vitamin D.

NMR spectrum: (CCl4) δ: 0.07(12H,S), 0.77(3H,S), 0.86 (9H,d,J=6 Hz), 0.90(9H,S), 0.96(9H,S), 3.30–4.10(2H,m), 4.70(1H,d,J=10 Hz), 5.00(1H,brs), 5.30(1H,brs), 5.56(1H,d,J=10 Hz)

mass spectrum (FD)m/e; 663(M−+1), 662(M−), 645, 627, 587, 530, 397, 339, 265

The reaction of Example 9 is expressed by the following formulas.

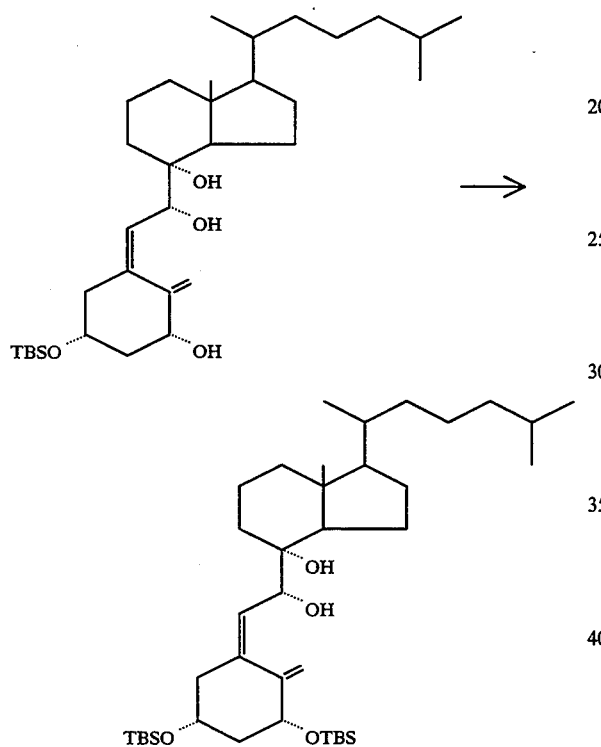

EXAMPLE 10

"Preparation of 1β-acetoxy.3β-O-(t-butyldimethylsilyl)-7,8-dihydroxy-7,8-dihydro vitamin D"

A 120 mg of 3β-O-(t-butyldimethylsilyl)-7.8-dihydroxy-7,8-dihydro-1β-hydroxy vitamin D, 2 ml of pyridine and an amount of 4-dimethylaminopyridine good for a catalyst were dissolved in 5 ml of methylene chloride and then 100 mg acetylchloride was added to the solution while it was being stirred at 0° C.

The solution of the reaction product was kept being stirred for 2 hours at room temperature and thereafter diluted by 30 ml of methylene chloride. The diluted solution was washed sequentially with water, 10% hydrochloric acid, saturated aqueous solution of sodium hydrogencarbonate and water and dried by sodium sulfate.

After removing the solvent, the residue was subjected to a process of silica gel column chromatography [silica gel 0.5 g, solvent: n-hexane-ethyl acetate (100:5 v/v)] to obtain 121 g of 1β-acetoxy.3β-O-(t-butyldimethylsilyl)-7,8-dihydroxy-7,8-dihydro vitamin D.

IR spectrum: ν max (CCHl3)cm−1: 3350, 1740

NMR spectrum: (CCl4) δ: 0.10(6H,S), 0.75(3H,S), 0.90(9h,d, J=6 Hz), 0.95(9H,S), 2.10(3H,S), 3.35–4.00 (1){,m), 4.70(1H,d,J=10 Hz), 4.60–5.00(1H,m), 5.05 (2Hbrs), 5.63 (1H,d,J=10 Hz)

mass spectrum: (FD) m/e; 573(M− −17), 530, 515, 489, 473, 325, 265

The reaction of Example 10 is expressed by the following formulas.

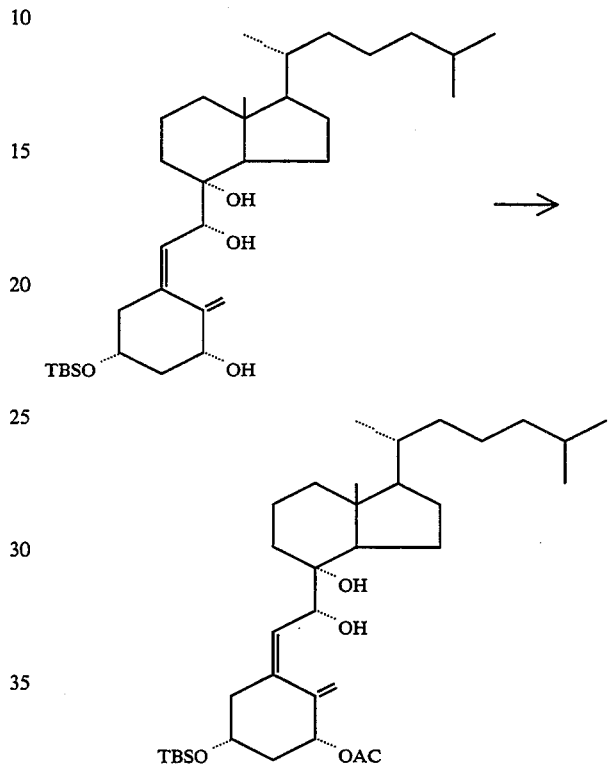

EXAMPLE 11

"Preparation of 3β-O-(t-butyldimethylsilyl)-1β, 7-diacetoxy-8-hydroxy-7,8-dihydro vitamin D"

A 100 mg of 3β-O-(t-butyldimethylsilyl)-7,8-dihydroxy-7,8-dihydro-1β-hydroxy vitamin D and an amount of 4-dimethylaminopyridine good for a catalyst were dissolved in 2 ml of pyridine and 100 mg of acetic anhydride was further added to the solution at 0° C.

The solution of the reaction product was stirred for two hours at room temperature and diluted with 50 ml methylene chloride. Thereafter, the diluted solution was washed sequentially with water, 10% hydrochloric acid, saturated water solution of sodium hydrogencarbonate and then dried by sodium sulfate.

After removing the solvent, the residue was subjected to a process of silica gel column chromatography [silica gel 0.5 g, solvent; n-hexane-ethyl acetate (100:3 v/v)] to obtain 110 mg of 3β-O-(t-butyldimethylsilyl)-1β,7-diacetoxy-8-hydroxy-7,8-dihydro vitamin D.

IR spectrum: ν max (CHCl4)cm−1: 3570, 1730

NMR spectrum: (CCl4) δ: 0.13(6H,S), 0.70(3H,S), 0.90(9H, d, J=10 Hz), 0.93(9H,S), 2.03(3H,S), 2.14 (3H,S), 3.50–4.10(1H,m), 4.80–5.00(1H,m) 5.40 (1H,d,J=10 Hz), 5.66 (1H, brs), 5.98 (1H, d, 10 Hz)

mass spectrum (FD) m/e; 632 (M−), 615, 573, 555, 367, 265

The reaction of Example 11 is expressed by the following formulas.

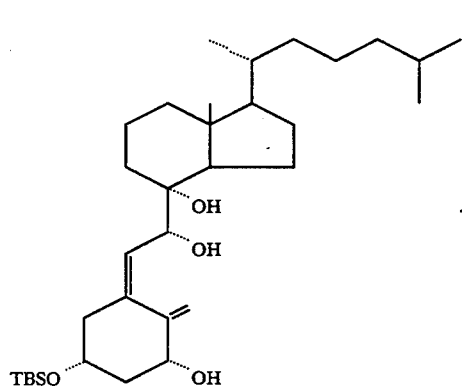 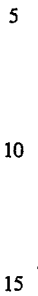 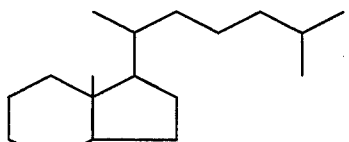 

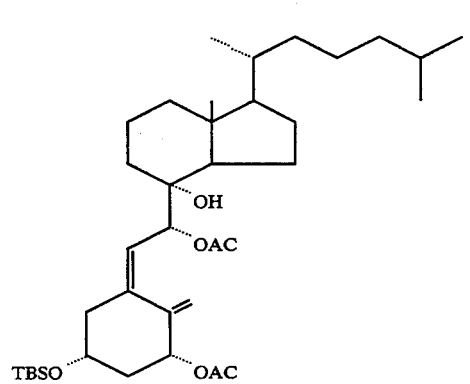 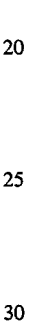 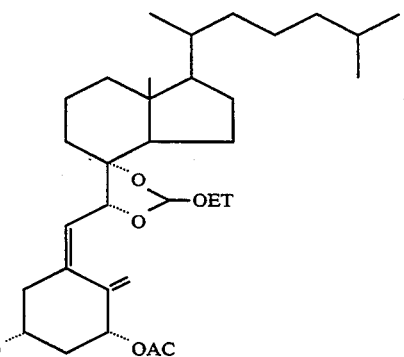

EXAMPLE 12

"Preparation of 1β-acetoxy-3β-O-(t-butylmethylsilyl)-7,8-O-ethoxymethylene-7,8-dihydroxy-7,8-dihydro vitamin D"

A 10 ml toluene solution containing 100 mg of 1β-acetoxy-3β-O-(t-butylmethylsilyl)-7,8-dihydroxy-7,8-dihydro vitamin D, 100 mg of ethylorthoformate and an amount of camphor sulfonic acid good for a catalyst were heated for 30 hours for reflux while it was being stirred in a Deam Stark apparatus.

After removing the solvent, the residue was subjected to a process of silica gel chromatography [silica gel 0.5 g, solvent; n-hexane-ethyl acetate (100:1 v/v)] to obtain 100 mg of 1β-acetoxy-3β-O-(t-butyldimethylsilyl)-7,8-O-ethoxymethylene- 7,8-dihydroxy-7,8-dihydro vitamin D.

IR spectrum: ν max (CHCl$_3$)cm$^{-1}$: 1730

NMR spectrum: (CCl$_4$) δ: 0.10(6(H,S), 0.50(3H,S), 0.87(9H, d, J=6 Hz), 0.90(9H,S), 2.13(3H,S), 3.50 (2H, q, J=10 Hz ), 3.50–4.00(1H,m), 4.66(1H,d, J=10 Hz), 5.00–5.20 (2H, m), 5.48 (1H,S), 5.70 (1H,d,J=10 Hz)

mass spectrum: (FD) m/e; 647 (M$^-$+1), 646(M$^-$), 600, 572, 556, 515, 501

The reaction of Example 12 is expressed by the following flormulas.

POTENTIAL INDUSTRIAL APPLICATIONS

Compounds according to the present invention are novel substances generally expressed by formula [II ] above. These substances typically include 1β,7,8-trihydroxy vitamin 1β,7,8,-trihydroxy vitamin D$_3$ and their derivatives that have many potential industrial applications as they can play a vital role in formation of bones because they can regulate absorption of calcium and reabsorption of inorganic substances by intestine. Moreover, they can be effective for inducing cell differentiation and also for curing such diseases as chronic nephric insufficiency and osteoporosis.

If compared with any known similar methods, the method according to the invention is industrially more efficient and effective for manufacturing novel chemical compounds generally expressed by formula [II] above as any of such compounds can be prepared by directly combining a compound expressed by formula [I] above with an oxygen function group at position C(1) through utilization of chemical reaction of allylic acid.

What is claimed is:

1. A chemical compound expressed by the formula

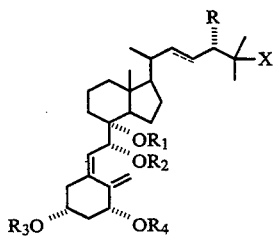

wherein
R represents a hydrogen atom or a methyl group and the dotted line along a side chain represents an optional additional C—C bond only when R is a hydrogen atom;
R$_1$, R$_2$, R$_3$, R$_4$ independently represent a hydrogen atom or a hydroxy protecting group; and
X represents a hydrogen atom or a hydroxy group.

* * * * *